(12) United States Patent
Shimp

(10) Patent No.: US 7,357,895 B2
(45) Date of Patent: *Apr. 15, 2008

(54) METHOD FOR STERILIZING BIOACTIVE MATERIALS

(75) Inventor: Lawrence A. Shimp, Morganville, NJ (US)

(73) Assignee: Osteotech, Inc., Eatontown, NJ (US)

( * ) Notice: Subject to any disclaimer, the term of this patent is extended or adjusted under 35 U.S.C. 154(b) by 363 days.

This patent is subject to a terminal disclaimer.

(21) Appl. No.: 10/250,661

(22) PCT Filed: Jan. 4, 2002

(86) PCT No.: PCT/US02/00102

§ 371 (c)(1),
(2), (4) Date: Dec. 19, 2003

(87) PCT Pub. No.: WO02/070024

PCT Pub. Date: Sep. 12, 2002

(65) Prior Publication Data

US 2004/0101958 A1    May 27, 2004

(51) Int. Cl.
*A61L 2/00* (2006.01)
(52) U.S. Cl. .......................................................... 422/1
(58) Field of Classification Search .................... 422/1; 435/1.1; 623/16.11
See application file for complete search history.

(56) References Cited

U.S. PATENT DOCUMENTS

| 2,962,380 | A | * | 11/1960 | Wertheim | ................... 426/240 |
|---|---|---|---|---|---|
| 5,485,496 | A | | 1/1996 | Lee et al. | ...................... 378/64 |
| 5,722,977 | A | | 3/1998 | Wilhelmy | |
| 5,730,933 | A | | 3/1998 | Peterson | ...................... 422/22 |
| 5,753,182 | A | | 5/1998 | Higgins | ....................... 422/23 |
| 5,782,914 | A | | 7/1998 | Schankereli | .................. 623/11 |
| 6,224,607 | B1 | | 5/2001 | Michelson | |
| 6,261,293 | B1 | | 7/2001 | Nicholson et al. | |
| 6,261,295 | B1 | | 7/2001 | Nicholson et al. | |
| 6,447,512 | B1 | | 9/2002 | Landry et al. | |
| 6,641,582 | B1 | | 11/2003 | Hanson et al. | |
| 6,692,501 | B2 | | 2/2004 | Michelson | |
| 6,755,839 | B2 | | 6/2004 | Van Hoeck et al. | |
| 6,840,941 | B2 | | 1/2005 | Rogers et al. | |
| 7,033,362 | B2 | | 4/2006 | McGahan et al. | |
| 7,083,625 | B2 | | 8/2006 | Berry | |

FOREIGN PATENT DOCUMENTS

| DE | 4125776 | 2/1993 |
|---|---|---|
| EP | 0424129 | 4/1991 |
| WO | 96/40297 | 12/1996 |
| WO | 98/31403 | 7/1998 |

OTHER PUBLICATIONS

The terms "substantial" and "fully"-Merriam-Webster Online Dictionary, at the web- http://m-w.com, pp. 1-2, Nov. 17, 2006.*

* cited by examiner

*Primary Examiner*—Sandra E. Saucier
*Assistant Examiner*—Satyendra K. Singh
(74) *Attorney, Agent, or Firm*—Kenneth E. Levitt; Dorsey & Whitney LLP

(57) ABSTRACT

A method is provided for sterilizing a bioactive material which comprises contacting the bioactive material with hydrogen gas and while the bioactive material is in contact with hydrogen gas, irradiating the bioactive material with ionizing radiation to sterilize the material.

7 Claims, No Drawings

METHOD FOR STERILIZING BIOACTIVE MATERIALS

BACKGROUND OF THE INVENTION

This invention relates to a method for sterilizing bioactive, i.e., biologically active, materials employing ionizing radiation such as gamma, electron beam and x-ray radiation.

It can be difficult to sterilize a bioactive material, e.g., living tissue, many kinds of proteinaceous substances, drugs, etc., intended for medical/surgical application without negatively affecting the therapeutically useful properties of the material to a significant degree. For example, changes in pH, ionic strength or temperature can result in reversible or irreversible changes in the character of many kinds of bioactive materials and, consequently, a diminution in their therapeutic effectiveness. Attempts have been made to avoid or minimize irreversible changes to bioactive materials by sterilization employing ethylene oxide. However, ethylene oxide often reacts with proteins. In addition, because of the known tissue toxicity and the carcinogenic potential of the by-products of ethylene oxide, the United States Food and Drug Administration has set maximum residue limits for ethylene oxide and its major reaction products ethylene glycol and ethylene chlorhydrin.

Unlike ethylene oxide, radiation sterilization has the advantages of high penetrating ability, relatively low chemical reactivity and instantaneous effects without the need to control temperature, pressure, vacuum, or humidity. Radiation sterilization is a very convenient method for sterilizing medical devices, tissue, food, etc., and is widely used in industry. Both dosage levels and its biological effects are well known. It is generally believed that gamma-rays, electron beams, and x-rays as sources of ionizing radiation are equally effective in killing or inactivating microbial organisms. However, radiation can cause damage to the bioactive materials being sterilized. The damage can result from direct damage caused by the impact of radiation particles with proteins (resulting in broken chemical bonds), or, more commonly, from secondary reactions, usually activated oxygen, e.g., peroxides and oxygen radicals, that are generated by the interaction of the radiation and the material being sterilized. Many of these radicals are oxidizing in nature and do their damage by acquiring electrons from other substances resulting in cross-linking, radical chain reactions and bond breaking.

A variety of methods have been used to control radiation damage. For example, bioburden is controlled to minimize the radiation dosage required for sterilization. Also, because oxygen is a major source of reactive species formed upon irradiation, removing oxygen from the material to be irradiated can reduce the amount of secondary damage. Oxygen removal is accomplished by evacuating and sealing the package, evacuating and backfilling the package with a less reactive gas and then sealing the package, or by flushing the package with a less reactive gas before sealing. The most frequently used less reactive gas is nitrogen, but others such as argon, etc. have also been used. Oxygen removal, while beneficial, is not completely effective because reactive species can be generated by the action of radiation on water, oxygen containing compounds, etc., that are part of the bioactive material being sterilized.

Other efforts to minimize the damage to bioactive materials caused by radiation sterilization have included the use of free-radical scavengers such as, e.g., tocopherol, citric acid, butylated hydroxyanisole, butylated hydroxy toluene, tertiary butylhydroquinone, propyl gallate, ascorbate, and other antioxidants that are "generally recognized as safe" by the Food and Drug Administration. However, these free-radical scavengers may also form undesirable reactive species as a result of the sterilization process.

Lowering the temperature at which sterilization is carried out has also been resorted to. Liquids, when present, are frozen. However, attempts using solutions or other compounds to minimize the effects of free-radical formation during sterilization have had limited success due to the immobility of the compound at the temperatures at which sterilization commonly takes places, e.g., −70° C.

Thus, there remains a need for a method for protecting bioactive materials against the undesirable effects that frequently occur as a result of the sterilization process.

Therefore, it is an object of the invention to provide a method for protecting bioactive materials during radiation sterilization that will avoid or minimize negatively affecting the therapeutically useful properties of the materials to a significant extent.

It is a further object of the invention to provide a method for reducing the formation of undesirable chemically reactive species within a bioactive material undergoing radiation sterilization.

It is still another object of the invention to provide a method for the radiation sterilization of therapeutically useful proteinaceous substances and/or living tissues such as allograft bone and bone-derived materials which contain a variety of biologically active proteinacious components.

It is yet another object of the invention to provide a combined packaging and sterilizing method for a bioactive material.

BRIEF SUMMARY OF THE INVENTION

In keeping with these and related objects of the invention, there is provided a method for sterilizing a bioactive material which comprises contacting the bioactive material with hydrogen gas and while the bioactive material is in contact with hydrogen gas, irradiating the bioactive material with ionizing radiation to sterilize the material.

The foregoing method is conveniently utilized for the concurrent packaging and sterilization of a wide variety of bioactive materials. Thus, e.g., a package containing a bioactive material such as allograft bone for implantation, demineralized allograft bone, etc., can be evacuated and backfilled with hydrogen gas or mixture of hydrogen gas and a less reactive, preferably inert, gas such as nitrogen and the contents of the package sterilized by exposure to ionizing radiation such as gamma rays.

The expression "bioactive material" shall be understood herein to apply to any medically/surgically useful substance or device having a therapeutic action directly involving at least one biological mechanism and is to be distinguished from a biologically inert substance or device whose medical/surgical usefulness is essentially of a physical or mechanical character. Expressly excluded from the foregoing definition of "bioactive material" is a substance or device which is fabricated entirely from one or more biologically inert materials such as ceramic, synthetic polymer, etc., which when placed within the body is intended to function in a purely mechanical way, as for example, is the case with various kinds of prosthetic implants, surgical sutures, surgical clips, surgical meshes, fixation plates, fixation pins and screws, and the like.

The terms "sterilizing", "sterilization" and terms of like import shall be understood herein to mean a significant reduction in the bioburden of a bioactive substance by the destruction and/or inactivation of microorganisms, particularly pathogenic bacterial and viral microorganisms, and polynucleotide fragments thereof present upon and/or within the bioactive substance.

DETAILED DESCRIPTION OF THE INVENTION

The method of sterilizing of the present invention is applicable to a wide variety of bioactive materials which include living tissues such as human donor bone for implantation, partially and fully demineralized bone materials prepared therefrom and devices and compositions containing such materials, proteins such as keratins, collagens, albumens, globulins, hormones, enzymes, peptides, polypeptides, simple and conjugated proteins such as glycoproteins, mucoproteins, lipoproteins, heme proteins and nucleoproteins, growth factors such as transforming growth factor, epidermal growth factor and platelet-derived growth factor, bone morphogenetic proteins, cells such as bone marrow cells and mesenchymal stem cells, and the like. Especially preferred bioactive materials are the numerous known fully mineralized, partially demineralized and substantially fully demineralized autograft, allograft and xenograft cortical, cancellous and corticoncancellous bone implantable devices and compositions which possess osteogenic and/or osteoinductive properties.

The terms "osteogenic" as used herein shall be understood to refer to the ability of a material or substance to induce new bone formation via the participation of living cells from within the substance and "osteogenesis" as the mechanism or result.

The terms "osteoinductive" as used herein shall be understood to refer to the ability of a material or substance to recruit cells from the host which have osteogenic potential and the ability to form ectopic bone and "osteoinduction" as the mechanism or result The ionizing radiation which is employed in the sterilization of the bioactive material in accordance with the invention is essentially a beam of very high velocity, very small particles. The particles of the radiation beam interact with the bioactive material by colliding with the particles that make up the atoms of the material. That is, the particles of the radiation beam physically knock particles from atoms due to collision forces. These affected atomic particles are of two general classes, nuclear, which are found in the core of the atom, and electrons, which are found in the outer layers of the atom or molecule.

Nuclear particles consist of protons and neutrons. The energy required to disrupt nuclear particles is much greater than that found in chemical reactions and so nuclear particles are inert for chemical purposes. Disruption of the nucleus by radiation often makes the material permanently radioactive, and therefore sterilization radiation is held to energies below this threshold. Electrons participate in chemical reactions and much less energy is required to disrupt these than to disrupt the nuclear particles. Most of the effects of sterilizing radiation are concentrated on the electrons. The effects of sterilizing radiation, therefore, are chemical in nature, resulting in new or altered chemical compounds, but not in radioactive substances.

The three types of ionizing radiation used for sterilization are: gamma, electron beam (E-beam) and X-ray. Gamma radiation, usually from a cobalt 60 source, consists of very small particles (photons) which are fragments from the nucleus. Gamma radiation is non-directional, i.e., it goes everywhere, and never shuts off. This property makes it extremely dangerous to use. The advantage is that it has high penetrating power (several centimeters), yet a low enough energy that the danger of nuclear changes in the substance being treated is non-existent. E-Beam radiation consists of electrons accelerated by an electric field. The energy depends on the magnitude of the accelerating voltage and energies are usually expressed in units of million electron volts (Mev). The advantage of E-beam over gamma rays is that, being electrically generated, the radiation is only present when the electric power is turned on. In addition, the beam is directional and its position can be easily controlled by electric and magnetic fields. The disadvantage is that electrons are very large compared to gamma particles so E-beams do not penetrate deeply (several millimeters at most) and are best suited for thin materials such as milk flowing over a plate in a shallow stream. In addition, high energy E-beams (over 10 Mev) can cause nuclear changes, so sterilizing doses are always set for a lower energy.

X-rays consist of nuclear particles (a type of photon) that are somewhat between electrons and gamma particles in their properties. X-rays are generated by a high energy electron beam hitting a metal target and ejecting X-ray particles from the nuclei of the atoms in the target. The energy of the beam depends on the target composition and the E-beam energy. Much power is wasted in converting an E-beam to X-rays. However, compared to the original electrons, the X-ray particles are smaller, therefore, they have a higher velocity and penetrate more deeply. For sterilization purposes, they are restricted to 5 Mev or less. X-rays, because of their greater penetrating power, are more suited for sterilizing larger, denser objects than E-beams. Yet X-rays still retain the advantages of being electrically generated.

The above discussion refers to the primary radiation source. However, the impact of a radiation beam also leads to secondary collisions, i.e., secondary radiation. The electrons ejected from the primary collisions go on to collide with other electrons, and these electrons collide with still more electrons. There is thus a cascade effect and electrons cause most of the collisions, no matter what the primary beam is composed of.

It is understood that bioactive materials can be effectively sterilized by gamma, electron-beam, or X-ray radiation. Common sources of photon radiation are gamma sources and X-ray sources. The reason that the sources of radiation may be interchanged is that both photons and electrons interact with matter by electrical ionization and excitation reactions. The mechanisms of the interactions of the gamma rays and X-rays are different from the interactions of electron beams. It is well known that gamma rays and X-rays are electromagnetic waves frequently referred to as photons. Having no electric charge or mass, photons transfer energy to materials mainly through Compton scattering and, at low energies, through photoelectric absorption. In contrast to photons, electrons have both mass and charge, so they interact readily with other charged particles, transferring their kinetic energy to materials via numerous elastic and inelastic collisions. Therefore, circumstances do exist where one or the other type of irradiation source (photon or electron) is preferred. For example, gamma sterilization or X-ray is often preferred when the bulk density of the material is high or when high-density regions may shield other parts of the material from exposure to electrons.

Although radiation has little direct effect on proteins, radiation damage to tissue can still occur due to secondary effects. In addition to direct hits by radioactive particles, damage can be caused by heating and the formation of free radicals. Heating tends to be a local effect and can be minimized by using evenly penetrating forms of radiation and not using excessive doses. For example, electron beam radiation generates much more heat than gamma or X-ray radiation. Unfortunately, free radicals are much more difficult to control than heating. The secondary effects that damage tissue also theoretically enhance the effects of radiation in bringing about sterilization. However, controlling these effects to minimize radiation damage to desirable tissue has little practical effect on sterilization efficiency because dosage requirements are based only on the probability of direct hits on contaminating organisms. Secondary effects are too variable to be taken into account in official dose guidelines.

Radiation causes its damaging secondary effects primarily through the chemical activity of free radicals. The easiest to form radicals are oxygen, or oxygen containing radicals. Oxygen sources can be oxygen from the air, oxygen from water, or other oxygen containing substances. Oxygen radicals form peroxides, and the peroxides react readily with a large variety of substances. Such reactions often lead to cross-linking, which can alter the physical as well as the chemical state of proteins. Because configuration is just as important as chemical composition for protein function, cross-linking seriously damages proteins. In addition, if the oxygen is from an organic material, the site that the oxygen came from can also react and lead to further damage. Although the actual chemistry may be complex, it is not novel. Damage by radiation produced peroxides follows the same mechanisms as damage from sterilization by peroxide solutions or electrically generated ozone.

Although it is not entirely understood how hydrogen gas can act as a radical scavenging agent and/or reducing agent, the following theory is offered by way of a possible explanation. Radiation particles have a thermal energy level equal to several thousand ° C. and the radicals they produce also have thermal energies in the 1,000° C. range. The energies of the radicals and secondary ions are more than sufficient to initiate a reaction with hydrogen. It is in this way that hydrogen can help to control unwanted side reactions arising from sterilizing radiation. The hydrogen acts as a reducing agent and radical scavenger that actively neutralizes destructive radicals as they form. The advantage to using hydrogen in the sterilization method herein is that hydrogen can help to neutralize destructive species that originate from within the irradiated bioactive material itself. Oxygen removal alone cannot address damage from these sources. A further advantage of using hydrogen is its ability to easily diffuse throughout most bioactive materials and therefore be present at the sites of radical formation, even in solidly frozen objects or high density objects such as donor bone for implantation. Hydrogen remains in its gaseous state to temperatures as low as −259° C. at standard pressure. By contrast, at low temperatures, conventional antioxidants are frozen and immobile, so they cannot always be present at the sites of radiation damage (initiation and/or progression). Also, hydrogen's small size, i.e., a bond length of about 0.75 Å, allows it to penetrate the small pores of the item to be sterilized.

Because it remains mobile at low temperatures, the presence of hydrogen during the irradiation operation is especially advantageous in the case of bioactive materials which are below ambient temperature, e.g., at from about 10° C. to about −196° C. (liquid nitrogen) and preferably from about 0° C. to about −78° C. (solid carbon dioxide). Freezing the bioactive material, e.g., allograft bone or bone-derived product, prior to exposing the material to radiation can be a useful expedient to further guard against the formation of free radicals as the frozen material is undergoing irradiation.

Although hydrogen has a much higher activation energy compared to conventional antioxidants or radical scavengers, during irradiation, as explained above, there is more than enough energy to initiate a reaction with hydrogen. An advantage of hydrogen is that it is not destroyed by radiation; at worst it dissociates into hydrogen radicals that quickly recombine or form a harmless compound with a nearby organic material. By contrast, conventional organic antioxidants/radical scavengers can break into non-functional fragments, or, once fully oxidized, become very powerful oxidizing agents themselves.

The hydrogen can be combined with a diluent gas, e.g., a less reactive, and preferably inert, gas such as nitrogen, helium, argon, xenon, or similar gases or mixtures of gases. Such gases are commercially available, e.g., from laboratory supply companies, and are generally provided, for example, as pressurized cylinders. When diluted with a less reactive or inert gas, hydrogen can be present at concentrations of from about 5 to about 80% by volume and preferably from about 30 to about 70% by volume.

The pressure of the hydrogen gas/hydrogen and inert gas mixture can be at, above or below ambient. When the method of the invention is carried out upon a bioactive material contained within a package, e.g., as hereinafter described, elevated gas pressures can be employed up to those that can be withstood by the package system. In general, ambient pressure to pressures on the order of up to about 3 atmospheres can be utilized.

The method of the invention herein can be carried out by evacuating a package containing the bioactive material to be sterilized, backfilling the package with hydrogen or hydrogen-insert gas mixture, and sealing the package. The evacuation and backfilling cycles can be repeated any number of times.

The package can be made of any reasonably non-porous material, though the less permeable the package is to hydrogen, the longer the delay can be from when the package is filled until the radiation process is carried out. The main purpose of packaging is to protect the sterility of the bioactive material contents. When a bioactive material is placed in its protective container and subsequently sterilized, the process is referred to as terminal sterilization. When the bioactive material is sterilized first and then placed in a presterilized container, the process is referred to as sterile filling. Packaging material used for terminal sterilization must permit full sterilant penetration as well as provide a microbial barrier. Consideration must also be given to the conditions to which the sterile package will be exposed until used, such as storage, transportation, frequency of handling, etc.

Storage time by itself is not expected to affect the maintenance of sterility. However, longer storage time may increase the incidence of potentially harmful conditions. Frequent handling, wetness, and possible deterioration of the packaging material are typical examples of conditions that may compromise sterility and limit the shelf life of a package. The package contents may have a specific shelf life. The wide choice of packaging materials and methods available for industrial processes allows the selection of packaging materials, package designs, and processes that provide maximum protection. Indeed, with appropriate packaging, sterilization methods, and materials, sterility can be protected for an indefinite length of time.

A preferred type of packaging system for use in the invention herein employs the so-called peel-open packages.

These are constructed by heat sealing two webs of packaging material around the edges. One layer is usually a plastic film of composite construction, that forms the heat seal, the other is a surgical-grade kraft paper designed to give an effective microbial barrier or a moisture impermeable plastic or metal foil that forms a moisture and a microbial barrier. Shelf life is extended to a time that is determined by need rather than sterility protection. Whichever packaging method is used, provisions must be made for the opening of the package and the retrieval of the sterilized bioactive material in a manner that does not compromise its sterility.

In a variation of the packaging procedure, the bioactive material can be sealed in a porous package, the porous package then placed in an outer non-permeable package, thus treating the porous packaged product with its contents of bioactive material as the material to be sterilized. In a further variation, several porous packaged items can be placed in a common non-permeable package that is evacuated and backfilled with hydrogen or hydrogen-inert gas mixture. The outer package can then be removed or retained as desired as long as the porous package still functions as a microbial barrier.

As an alternative to evacuation and backfilling, the package can simply be flushed with hydrogen gas, preferably with a hydrogen and inert gas mixture, prior to filling. However, this flushing technique does not remove trapped oxygen from the package as readily as the aforedescribed evacuation and backfilling operation.

In terms of the sterilization process, the hydrogen-gas packaged bioactive material can be exposed to ionizing radiation in an otherwise known and conventional manner.

Radiation sterilization, as currently practiced, employs electron accelerators or radioisotopes. Electrons have relatively low penetration ability, and the use of accelerators requires careful control. Gamma-radiation sterilization usually employs $^{60}$Co and occasionally $^{137}$Cs as the radioisotope source. A very wide range of packaging materials can be used because gamma rays possess a considerably greater penetrating ability. However, they must not be degraded to the point where the quality of the aseptic barrier is compromised.

Bioburden determinations can be carried out to determined. a desired radiation dose. Thus, the dosage of ionizing radiation for a specific bioactive material can be experimentally determined by measuring the bioburden of the pre-sterilized material employing known and conventional procedures so as to provide a typical range of initial bioburden for the material and thereafter irradiating portions of the material at different dosage levels and again measuring bioburden following termination of each radiation exposure. Based on these experimental data, an optimum radiation dosage level can be determined for a specific bioactive material and target bioburden endpoint. In these experiments, radiation exposure can be monitored with biological indicators utilizing *Bacillus pumilus* as the test organism. Counters and electronic measuring devices can also be used. Chemical dosimeters based on ferrous sulfate, ferrous cupric sulfate, or ceric sulfate are also generally useful. Color-change process indicators may be used but these cannot measure the radiation dose.

In general, the radiation exposure whether for gamma rays, E-beam or X-rays, can range from about 5 to about 50 KGy and preferably from about 10 to about 40 KGy depending on the nature of the bioactive substance to be sterilized, its initial bioburden and the desired bioburden endpoint.

It can be advantageous to expose the bioactive material to hydrogen gas/dilute hydrogen gas for some period of time prior to conducting the irradiating operation in order to allow the gas to achieve greater penetration, permeation or diffusion within the bioactive material before its exposure to ionizing radiation. Pre-radiation exposure times to the hydrogen gas/mixture of hydrogen and inert gas of from about one minute to about one week and preferably from about one hour to about two days are generally suitable in this regard.

It can also be advantageous to maintain contact of the bioactive material with the hydrogen gas/mixture of hydrogen and inert gas even after the irradiation operation has been terminated since the hydrogen gas will still continue to scavenge for any residual free radicals that may be present.

The foregoing descriptions of the preferred embodiments of the present invention have been presented for purposes of illustration and description. They are not intended to be exhaustive or to limit the invention to the precise forms disclosed, and obviously many other modifications and variations are possible in light of the above teachings. The embodiments were chosen and described to best explain the principles of the invention and its practical applications, thereby enabling others skilled in the act to best utilize the invention in its various embodiments and with various modifications as are suited to the particular use contemplated.

The following examples are illustrative of the method for sterilizing a bioactive material in accordance with the invention.

EXAMPLE 1

Posterior intervertebral ramp implants are produced in a clean room environment from human femurs. The finished implants are washed in 70% ethyl alcohol, lyophilized (freeze-dried) and placed in individual tray packages.

Each tray is placed in an Audionvac sealing apparatus (Audion Eleetro B.V., Weesp-Holland) which is supplied with a cylinder consisting of 50/50 hydrogen/argon gas. Before the tray packages are sealed, they are evacuated and backfilled with the gas mixture twice. Following sealing, the gas mixture remains in each tray package.

The packaged implants are then sealed packages and then treated with 15 KGy gamma radiation from a cobalt 60 source to reduce the bioburden of the implants to the desired levels.

EXAMPLE 2

Posterior intervertebral ramp implants as described in Example 1 are placed in individual tray packages provided with porous lids to provide ready transfer of gases out of and into the packages. The tray packages are then placed in an Audionvac sealing apparatus supplied with a source of substantially pure nitrogen gas. Each tray is evacuated and backfilled with nitrogen gas twice to replace the air (containing oxygen) with essentially pure nitrogen gas. Each sealed tray is then placed in a second larger tray, the trays are placed in an Audionvac sealing apparatus supplied with a source of substantially pure hydrogen. The trays are evacuated and backfilled twice with hydrogen gas before being sealed. This step results in each sealed package possessing a hydrogen-rich atmosphere which diffuses into the implant contained therein. Irradiation of the tray packages is then carried out as described in Example 1.

What is claimed is:

1. A method for sterilizing an osteogenic and/or osteoinductive bioactive material for implantation within a human body which comprises contacting the bioactive material with hydrogen gas in a sealed package, and while the bioactive material is in contact with the hydrogen gas, irradiating the bioactive material with ionizing radiation to sterilize the bioactive material, wherein contacting the bioactive material with the hydrogen gas comprises contacting the bioactive material with a gaseous atmosphere of about 100% hydrogen gas by volume.

2. The method of claim 1, wherein the bioactive material comprises at least one osteogenic and/or osteoinductive material selected from the group consisting of fully mineralized autograft bone, partially demineralized autograft bone, allograft bone, xenograft bone, cortical bone, cancellous bone, corticocancellous bone, and combinations thereof.

3. A method for sterilizing an osteogenic and/or osteoinductive bioactive material for implantation within a human body which comprises contacting the bioactive material with hydrogen gas in a sealed package, and while the bioactive material is in contact with the hydrogen gas, irradiating the bioactive material with ionizing radiation to sterilize the bioactive material, wherein contacting the bioactive material with the hydrogen gas comprises contacting the bioactive material with a gaseous atmosphere containing from about 5% to about 80% hydrogen gas by volume, the balance of the gaseous atmosphere being made up of one or more diluent gases or inert gases.

4. The method of claim 3, wherein the bioactive material comprises at least one osteogenic and/or osteoinductive material selected from the group consisting of fully mineralized autograft bone, partially demineralized autograft bone, allograft bone, xenograft bone, cortical bone, cancellous bone, corticocancellous bone, and combinations thereof.

5. The method of claim 3, wherein contacting the bioactive material with the hydrogen gas comprises contacting the bioactive material with a gaseous atmosphere containing from about 30% to about 70% hydrogen gas by volume, the balance of the gaseous atmosphere being made up of one or more diluent gases or inert gases.

6. The method of claim 5, wherein the diluent gas or inert gas is at least one of nitrogen or argon.

7. The method of claim 3, wherein the diluent gas or inert gas is at least one of nitrogen or argon.

* * * * *